United States Patent
Okumura et al.

[11] 3,973,271
[45] Aug. 3, 1976

[54] SEMICONDUCTOR DEVICE HAVING BONDING PADS EXTENDING OVER ACTIVE REGIONS

[75] Inventors: Tomisaburo Okumura; Takatoshi Matsuo, both of Kyoto, Japan

[73] Assignee: Matsushita Electronics Corporation, Osaka, Japan

[22] Filed: Apr. 28, 1971

[21] Appl. No.: 138,311

Related U.S. Application Data

[63] Continuation of Ser. No. 782,353, Dec. 9, 1968, abandoned.

[30] Foreign Application Priority Data
Dec. 13, 1967 Japan............................. 42-80214

[52] U.S. Cl............................ 357/34; 357/35; 357/65; 357/67; 357/68
[51] Int. Cl.².................. H01L 23/48; H01L 29/72; H01L 29/46; H01L 29/62
[58] Field of Search............. 317/235, 40.12, 40.13, 317/234, 5.2, 5.3, 5.4

[56] References Cited
UNITED STATES PATENTS

| | | | |
|---|---|---|---|
| 3,191,070 | 6/1965 | Jones et al. | 17/235 Z |
| 3,204,321 | 9/1965 | Kile | 317/234 J |
| 3,237,271 | 3/1966 | Arnold et al. | 317/234 J |
| 3,287,610 | 11/1966 | Reber | 317/234 |
| 3,290,570 | 12/1964 | Cunningham | 317/234 |
| 3,361,592 | 2/1968 | Quetsch, Jr. et al. | 117/212 |
| 3,363,150 | 1/1968 | Whitman et al. | 317/234 |
| 3,373,323 | 3/1968 | Wolfrum et al. | 317/235 Z |
| 3,390,025 | 6/1968 | Strieter | 317/235 Y |
| 3,431,468 | 3/1969 | Huffman | 317/101 |
| 3,443,173 | 5/1969 | Tsang et al. | 317/235 Y |
| 3,457,631 | 7/1969 | Hall et al. | 317/235 Z |
| 3,462,349 | 8/1969 | Gorgenyi | 204/15 |
| 3,471,755 | 10/1969 | Bilotti | 37/235 Z |
| 3,473,979 | 10/1969 | Haenichen | 317/235 Y |
| 3,483,440 | 12/1969 | Dulin | 317/234 |
| 3,489,964 | 1/1970 | Masuda | 317/235 Z |
| 3,496,427 | 2/1970 | Lee | 317/234 |
| 3,496,427 | 2/1970 | Lee | 317/234 |

Primary Examiner—Andrew J. James
Attorney, Agent, or Firm—Stevens, Davis, Miller & Mosher

[57] ABSTRACT

A high-frequency transistor of planar structure having emitter and base regions of extremely fine structure to reduce the junction capacity. For the wire bond connection between said emitter or base region and an external lead wire, the transistor has the aluminium electrodes which swell and extend on the insulating film.

2 Claims, 4 Drawing Figures

INVENTOR

BY

ATTORNEY

SEMICONDUCTOR DEVICE HAVING BONDING PADS EXTENDING OVER ACTIVE REGIONS

This application is a continuation of application Ser. No. 782,353, filed Dec. 9, 1968, now abandoned.

This invention relates to a semiconductor device, and more particularly to the structure of a planar transistor.

In a transistor for high-frequency above VHF region, in order to reduce the collector junction capacitance an expedient of decreasing the area of the base diffused region without shortening the effective length of the emitter has been employed. For example, emitter and base metal electrodes are extended to some portions distant from the active regions of transistor or to some portions of the insulating film on the collector region in such a sense as to form swollen portions at the extended portions. Such a swollen portion is called a bonding pad and serves as a connecting point for the external lead.

It is necessary that the emitter region has a narrow width in order not to harm the high-frequency characteristic. But it is difficult to fit by pressure bonding an external thin wire to the portion of metal electrode just on the emitter region.

Besides, a transistor with the above structure shows deterioration in characteristics when it is sealed in plastics. Invasion of water dissolves or erodes the aluminium electrode and causes disconnection.

This invention is aimed at solving the above-mentioned problems, and provides a high-frequency semiconductor device with a structure free from any disconnection even when the metal electrode vanished by dissolution. The semiconductor device of this invention is of a planar type having metal thin film electrodes connected to the base and emitter regions, and swollen portions or bonding pad portions for the connection of external lead wires extending from the metal thin film electrodes towards an insulating film on the top of substrate. The device is characterized in that parts of the base and emitter doping regions extend towards just under the bonding pad portions and make ohmic contacts therewith.

In the above semiconductor device or transistor of this invention where the base and emitter doping portions extend partially towards just under the metal bonding portions, contact windows similar to those for metal electrodes are provided at the bonding pads so that the wire bonding process allows the doping regions to be connected with the external thin lead wires, e.g. gold, directly or through the metal electrodes. Therefore, even if the metal thin film electrodes vanished by erosion at the thin portion, the electric connection of the base and emitter doping regions with the respective external electrodes are still maintained.

In the above structure although the collector junction capacity increases more or less due to the elongation of the diffused regions, this can be minimized by decreasing the width of the extended diffused regions. By doing so any trouble in practical use is avoided.

Other objects, features and advantages of the present invention will be readily apparent from the following detailed description of certain preferred embodiments taken in conjunction with the accompanying drawings, in which.

Figure 1:
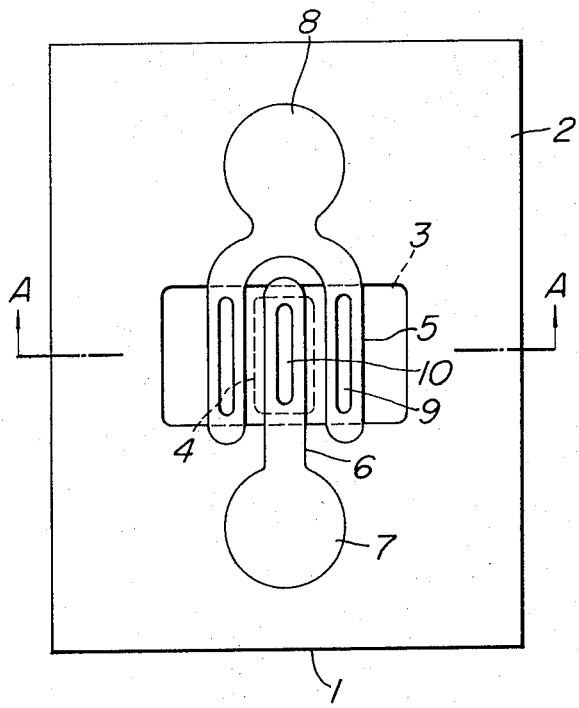
FIG. 1 is a plane view showing an example of a prior art planar type transistor.
Figure 2:
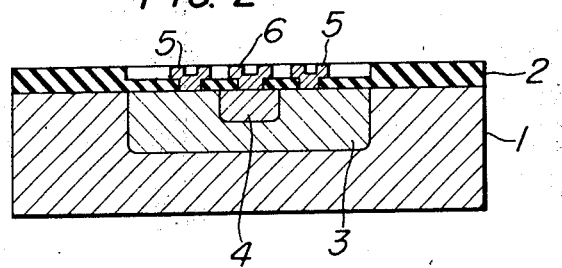
FIG. 2 is a cross-sectional view along the line A — A in FIG. 1.

In FIGS. 1 and 2, a prior art bonding pad structure for the connection of external lead wires is shown. The transistor is formed in the following manner. A thin oxide film 2 is formed on a prescribed substrate 1, e.g. silicon semiconductor substrate. A small window is provided in the oxide film by using the well-known photolithographic process. Impurity is diffused through this window into the silicon substrate thereby to form a base diffused region 3. An emitter diffused region 4 is formed in the base region substantially in the same manner. Metal thin films such as aluminium are coated on the base region 3 and the emitter region 4 by vacuum evaporation thereby to form a base electrode 5 and an emitter electrode 6 having ohmic contacts. Metal thin wires are bonded by pressure on the metal electrodes 5 and 6 for external connection. When the slender rectangular emitter 4 is formed in the rectangular region 3, it is necessary that the emitter region 4 has a narrow width in order not to harm the high frequency characteristic. It is difficult, therefore, to fit by pressure bonding an external thin wire, e.g. gold, to the portion of metal electrode 6 just on the emitter region. The metal electrode extends from the emitter diffused region to the top of the collector, at which the bonding pad 7 is provided. A thin wire, e.g. gold, is bonded by pressure on this portion to lead it to an external lead terminal. 8 is a bonding pad portion of the base electrode. The extended portion and bonding pad portion of these metal electrodes are completely insulated from each other by the insulating film 2. The connection between the base diffused region 3 and the metal electrode 5 and between the emitter diffused region 4 and the metal electrode 6 are made on the contact windows 9 and 10 respectively.

A transistor with the above structure shows deterioration in characteristics when it is sealed in plastics. Plastic materials not only allow essentially a small degree of osmosis of water but also suffers from invasion of water from the gaps between the plastic and lead wires. If the moisture reaches the transistor element, various characteristics are deteriorated. Among the deteriorations, the most serious one is the disconnection of metal electrodes or aluminium deposition layers. The invading water dissolves the aluminium layers and causes disconnection. Disconnection of aluminium electrodes by erosion or dissolution occurs occasionally, particularly in the structure where the bonding pad is formed on the collector insulating film and the emitter or the base region is connected with the bonding pad by slender metal electrodes. It is inferred that such erosion or dissolution is ready to occur either when the invading water contains active materials or active ingredients existing in the plastic are mixed with the invading water, or whenharmful impurities deposited on the surface of a transistor element before sealing are dissolved in the invading water.

According to this invention, portions of emitter and base doping regions are extended as far as the bottom of the bonding pads. Contact windows are provided right under the bonding pads for forming contact portions. Therefore, even when the surface portion of a metal electrode vanishes due to erosion or mechanical action, durable use is possible without harming the electrical characteristics. The semiconductor device of this invention is not limited to a transistor of planar structure, but can be applied to an integrated circuit means, particularly to an element sealed by plastics.

The invention will be explained in more detail with reference to the embodiments.

Figure 3:
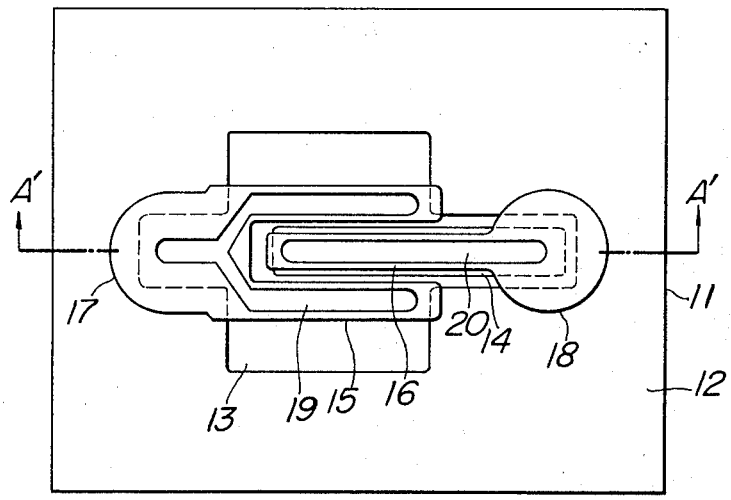
FIG. 3 is a plane view showing an example of a semiconductor device according to this invention.
Figure 4:
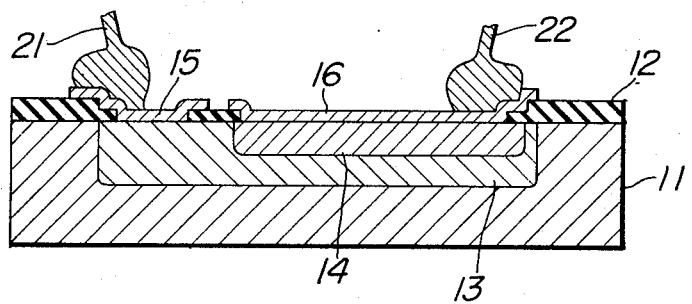
FIG. 4 is a cross-sectional view along the line A' — A' in FIG. 3.

In FIGS. 3 and 4, 11 is an N type silicon substrate, 12 is a silicon oxide film, 13 is a base diffused region with P type conductivity, 14 is an N type emitter diffused region. 15 and 16 are base and emitter metal thin film electrodes formed by vacuum evaporation of aluminium. As is evident in these figures, the metal electrodes 15 and 16 extend as far as the bonding pads 17 and 18. The contact windows 19 and 20 extend as far as the bonding pad portions. In FIG. 4 external lead wires, gold, 21 and 22 are bonded by pressure mounting on the contact windows.

The inventor's experiment shows that a high frequency transistor with a good durability is obtainable in the following case:

More than 50% of the total area of bonding pad portion extends on the insulating film and the other portions are in ohmic contact with the diffused regions extended from the base and emitter active regions which form the main active regions of a transistor. The external lead wires are connected to the ohmic contact portions.

If the effective emitter length is designed to be equal to that of a prior art one shown in FIGS. 1 and 2, no substantial difference is seen in the high frequency characteristic. However, in a boiling test for 200 hours in water 10 out of 40 prior art samples suffered disconnection due to the dissolution of electrodes while none of 50 samples of this invention suffered any disconnection. Although in the above embodiment the contact windows are continuous from the emitter or base active region to the bonding pads, the same result is obtainable if the contact window is divided into two or more parts.

The after-effect of the disappearance of aluminium electrodes in the inventive transistors which have completed the wire bonding is examined by removing the exposed aluminium layer by using chemical etching. The results show that all the samples are satisfactory without any disconnection. Electrical characteristics after the test are as shown in the following table. No particular harm is seen except a certain increase in the base resistance.

|  | without removing aluminium | removing aluminium |
| --- | --- | --- |
| current gain $h_{FE}$ | 150 | 155 |
| collector capacitance Cre(pF) | 1.15 | 1.11 |
| base resistance Zrb($\Omega$) | 35 | 68 |
| transition frequency $f_T$(MHz) | 240 | 235 |

What is claimed is:

1. A planar type semiconductor device comprising a semiconductor body, base and emitter regions formed in one surface thereof, an insulator layer on said one surface, said insulator layer having apertures for electrode attachment to said base and emitter regions, and electrodes comprising a metallic film ohmically contacting said base and emitter regions through said apertures, said electrodes having narrow extensions and generally circular bonding pads extending over said insulating layer at the extremities of said extensions, said base and emitter regions and apertures having narrow extensions extending to beneath said bonding pads, wherein lead wires are bonded to said extensions of said base and emitter regions at said bonding pads.

2. A planar type semiconductor device according to claim 1, wherein more than 50% of the total area of each of said bonding pads extends over said insulating layer.

* * * * *